(12) United States Patent  
Anderer (10) Patent No.: US 7,131,989 B2  
(45) Date of Patent: Nov. 7, 2006

(54) APPARATUS AND METHOD FOR APPLYING A SEQUENCE OF THERAPEUTIC LIGHTS TO SPECIFIC POINTS ON A PATIENT'S BODY

(76) Inventor: Laura Anderer, 1364 Westchester Dr. W., West Palm Beach, FL (US) 33417

( * ) Notice: Subject to any disclaimer, the term of this patent is extended or adjusted under 35 U.S.C. 154(b) by 278 days.

(21) Appl. No.: 10/605,212

(22) Filed: Sep. 15, 2003

(65) Prior Publication Data

US 2004/0181268 A1    Sep. 16, 2004

Related U.S. Application Data

(60) Provisional application No. 60/411,113, filed on Sep. 16, 2002.

(51) Int. Cl.  
*A61N 5/01* (2006.01)
(52) U.S. Cl. .......................................... 607/88; 607/91
(58) Field of Classification Search ............... D24/210; D26/60–61, 63–65, 102; 362/250, 287, 339, 362/403, 414, 418, 427, 572; 606/9–11; 607/88, 90–91

See application file for complete search history.

(56) References Cited

U.S. PATENT DOCUMENTS

| | | | | |
|---|---|---|---|---|
| 5,424,931 A | * | 6/1995 | Wheeler | 362/418 |
| 6,554,439 B1 | * | 4/2003 | Teicher et al. | 362/2 |
| 6,582,115 B1 | * | 6/2003 | Huang | 362/565 |
| 2002/0128695 A1 | * | 9/2002 | Harth et al. | 607/88 |
| 2003/0130709 A1 | * | 7/2003 | D.C. et al. | 607/88 |

* cited by examiner

*Primary Examiner*—Roy D. Gibsin (74) *Attorney, Agent, or Firm*—John C. Smith (57) ABSTRACT

A light therapy system that exposes specific light frequencies to specific points on a patient's body. The light varies both in frequency and in length of exposure. A broad range of light frequencies are intermittently directed to chakra points on a patient's body. Selected light frequencies are sequenced for each chakra point. An adjustable apparatus is provided which can simultaneously expose multiple locations, with the ability to align each lamp to a specific location and at a specific distance from the patient's body.

15 Claims, 6 Drawing Sheets

APPARATUS AND METHOD FOR APPLYING A SEQUENCE OF THERAPEUTIC LIGHTS TO SPECIFIC POINTS ON A PATIENT'S BODY

CROSS REFERENCE TO RELATED APPLICATIONS

This application is a non-provisional continuation of the commonly owned, and co-pending, provisional application entitled "Apparatus and Method for Applying a Sequence of Therapeutic Lights to Specific Points on a Patient's Body," filed Sep. 16, 2002, bearing U.S. Ser. No. 60/411,113 and naming Laura Anderer, the named inventor herein, as sole inventor, the contents of which is specifically incorporated by reference herein in its entirety.

BACKGROUND OF INVENTION

1. Technical Field

The present invention relates to therapeutic devices. In particular, it relates to a light therapy system which exposes the patient to a series of light frequencies, with each frequency applied to a patient for a particular time period and to a particular location on the patient's body.

2. Background

It is well-known in a variety of medical fields that light therapy can provide many therapeutic effects. For example, ultraviolet light has been used for the treatment of skin disorders such as psoriasis. Laser light has been used to treat wounds, to assist in the rapid healing of post surgical incisions, and has been found, along with non-coherent light, useful in the treatment of conditions such as alopecia. In addition, fluorescent lights are used to treat newborn infants exhibiting signs of jaundice.

It has been found that the application of light can stimulate natural processes within the body. For example, the application of light to the scalp can produce a variety of therapeutic results. There has been, for example, a substantial amount of research done on the use of laser energy to stimulate the bodies natural processes to heal wounds, apply skin therapy, etc. The advantage of using the coherent light of a laser is that coherent light tends to concentrate power such that a greater effect can result from the application of a particular energy level. However, non-coherent light will also produce therapeutic and healing results when applied to a patient. It only differs from coherent light in the sense that its energy is not concentrated in the form of laser beam.

Lasers have been widely used in the application light to the surface of a patient's body. In the case of lasers, low-power lasers may be used in a variety of therapeutic applications. For example, low-power lasers are used widely for a variety of cosmetic applications such as skin care, scar reduction, wound healing and the like. One of several factors associated with the use of lasers is that laser treatments tend to increase skin blood circulation. In fact, studies have shown that the application of laser energy to the skin of a user can increase skin blood circulation by more than fifty percent without significant changes in skin temperature. This results in the skin receiving a more abundant supply of nutrients, and in turn, the structures in the skin also receive a more abundant supply of nutrients and necessary materials from the body. Further, microscopic studies have shown laser energy increases circulation and oxygenation of the blood to the skin, and also increases cell replacement or regenerative activity. These factors help the skin to remain in a healthy condition. Research on the use of cold beam lasers indicates that application of a cold beam laser to an individual's scalp will normalize metabolism of tissues, improve trophism (blood cell nutrition), and assure a regular sebaceous secretion.

Another factor associated with the use of light therapy is "energization." Energization can be explained as follows: Light is energy. The application of high levels of light to the skin provides energy which is used by the cells in the skin to assist in the normal chemical processes performed by those cells. The scientifically agreed-upon term for this is photobiostimulation. The most common example of light converting into chemical energy is photosynthesis, where plants are fed via light converted into chemical energy. In a similar way, light penetrates into soft tissue and increases the action of adenosine triphosphate (ATP), a molecule that is a major carrier of energy from one reaction site to another in all living cells. By doing so, light increases the energy available to cells so they take in nutrients faster and get rid of waste products. Because of this benefit, scientists and physicians have been using low level laser devices over the past 30 years to accelerate wound healing and regenerate tissue.

It has also been found that stimulation of the skin using non-coherent light also produces beneficial results. In particular, non-coherent light will stimulate the skin such that the ability of the skin to nourish and regenerate itself is enhanced in the same manner as was done by the laser. As can be seen, light therapy has been used to improve a variety of physical conditions. Further, different frequencies of light have been shown to have varying effects of the body.

While laser devices produce more concentrated energy, they are also limited due to their very narrow frequency bandwidth. Non-coherent light has an advantage over lasers in that it provides a broad-spectrum of light energy for use by the patient's body. The broader frequency range maximizes the stimulation of the skin tissue.

Currently available devices tend to be narrow in scope. For example, low power laser devices are typically used for localized wound treatment, or for scalp treatments to improve hair growth. In addition to laser devices, variety of other light generation devices are used to promote health. For example, infrared lamps are used to treat an extended area of surface tissue with both heat and light, LEDs are used to project pulsed light onto a patient to increase immunity, ultraviolet lamps are used to apply UV light to an individual's scalp to promote hair growth, etc. While the prior art has provided these devices or treatment of localized areas of an individual's body, it would be desirable to have a device capable of treating and rejuvenating the entire body.

SUMMARY OF INVENTION

The present invention provides a method that exposes specific points on the patient's body to light. The light varies both in frequency and in length of exposure. By providing a broad range of light frequencies to a patient's body, the ability of the patient's body to rejuvenate itself is improved as a result of the body's response to the sequencing light exposure. In addition, an apparatus is provided which can simultaneously expose multiple locations, with the ability to align each lamp to a specific location and at a specific distance from the patient's body.

DETAILED DESCRIPTION

Prior to a detailed discussion of the figures, a general overview of the system will be presented. The invention is directed to a device which directs a broad-spectrum of light energy to specific points on an individual's body, which are commonly known as chekra points. To accomplish this, a multi-lamp assembly is provided which has seven independent lamps that are adjustable in three dimensions, and which are each designed to focus on a particular chakra point. The longitudinal and lateral adjustments allow the lamp to be used on individuals of different heights and frame widths. In addition, the adjustable lamp arms are in turn attached to a height adjustable stand which allows the lamps to be vertically adjusted to provide the ideal amount of light to a particular chakra point.

The purpose of the lights is to inject light of varying frequencies into the cells of the individual for the purpose of increasing cellular energy and vibration which in turn stimulates the natural rejuvenation of the cells. A variety of colors are selected which represent different light frequencies. In addition, the selected frequencies can be rotated such that the particular chakra point will receive light energy for more than one light frequency range. By filtering light by color, the light energy injected into the individual cells will be equal to, or very close to, the natural undamped frequency of those cells.

In addition to selecting light having particular frequency ranges, the system also pulses the lights for specific periods of time to maximize the effect of the light on the cellular material of the individual. In addition to pulsing the light, the system also pulses the light at different rates with different colors.

The system uses crystal filters in combination with color filters to narrow the bandwidth of the frequency projected onto the patient. In the preferred embodiment, the lamp assembly holds the lamp which projects light through a removable filter. The light exiting the filter is then directed through a crystal filter which directs the light to the chakra point of the patient. We turn now to a more detailed discussion of the figures.

Figure 1:
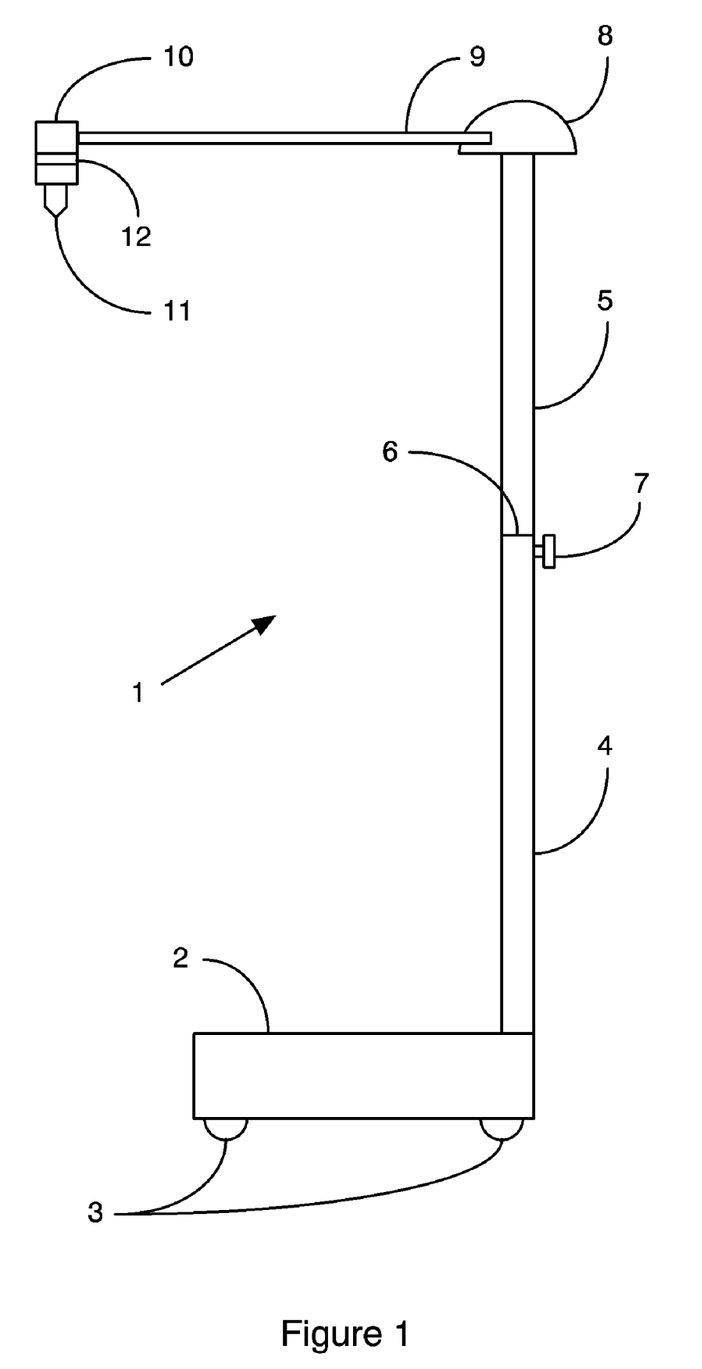
FIG. 1 is a diagram that illustrates a side view of a preferred embodiment of the light therapy device.

FIG. 1 is a side view of the preferred embodiment of the therapeutic lamp assembly 1. The therapeutic lamp assembly 1 includes a base section 2 which may be easily moved via attached wheels 3. Attached to the base section 2 is an adjustable vertical support 4, 5 which is comprised of a lower vertical support shaft 4 and an upper vertical support shaft 5. In the preferred embodiment the upper vertical support shaft 5 is slidably mounted within the lower vertical support shaft 4, and is inserted at the shaft opening 6 of the lower vertical support shaft 4. Retaining pin 7 is inserted through an aperture in lower vertical support shaft 4 and then through one of several apertures in the upper vertical support shaft 5. This allows the length of the adjustable vertical support 4, 5 to be adjusted such that the therapeutic lamp assembly I can be used for individuals of varying size, and also for individuals lying on surfaces at varying heights. Those skilled in the art will recognize that while the mechanism used to adjust the vertical elevation of the lamps can be fabricated as discussed above, any suitable method of adjusting the vertical height of the lamps can be used.

At the top of the upper vertical support shaft 5 is a head unit 8. The head unit 8 is securely attached to the top of vertical support shafts. In addition, a plurality of lamp arms 9 are attached to the head unit 8 ax the proximate ends of the lamp arms 9. Each lamp arm 9, at its distal end, has a lamp assembly 10 attached to it. Each of the lamp assembly's 10 have a lamp (not shown in this figure) mounted in the upper portion of the lamp assembly 10. Also shown on this figure is a color filter 12 which is inserted into a slot in the lamp assembly 10 for the purpose of providing a preliminary color filter for light projected by the lamp. After the color filtered light is output from the color filter 12, it then passes through a crystal 11 which further filters the light. The light emitted from the crystal 11 is then directed toward a particular chakra point.

In the preferred embodiment, the crystals 11 are clear quartz crystals which are cut such that they act as prisms which further select out specific frequencies. The selected frequencies (it, light colors) are directed to predetermined chakra points on a patient's body. Those skilled in the art will recognize that, if the crystals are properly cut, rotation of the crystals will direct a different light frequency (color) to the patient's body. Likewise, materials other than quartz may be used providing that they can function as a prism.

In the preferred embodiment, the control circuitry will be mounted in the base section 2 with the appropriate wiring fed through the adjustable vertical support 4, 5 and subsequently through the head unit 8, the lamp arms 9 and the lamp assemblies 10. The control circuitry pulses the lamp assemblies 10 on a periodic basis, and for a predetermined length of time for each pulse. Preferably the device will be powered by attachment to a conventional wall socket with the power supply also mounted in the base section 2. However, those skilled in the art will recognize that the device can also be battery powered, providing that sufficient room is provided within the base section 2 to contain the battery operated power supply.

In the preferred embodiment, the adjustable vertical support 4, 5 extends approximately 5.5 feet at its point of adjustment. The lower vertical support shaft 4 is preferably sized at approximately two inches in diameter. The wiring run through the vertical support 4, 5 can be any suitable wire, such as commercially available five to eighteen gauge wire. The lamp arms 9 extends outward from the head unit 8 such that the middle lamp arm 9 is approximately 18 inches long. Further, the lamp arms 9 are separated from one another at 22.5 degrees. The wires extending from the head unit 8 to the lamp assemblies 10 can be any suitable wire, such as two to eighteen gauge wire.

Those skilled in the art will recognize that while the above noted figures represent a preferred embodiment they are exemplary in nature and not critical to the invention. Furthermore, depending ante size of the individual being treated, the lengths of the anus and their relative angles may vary. Therefore, any suitable size may be used to accomplish the goals and purposes of the invention. Likewise, a lower vertical shaft 4 and the upper vertical shaft 5 can be secured together by any suitable means. While the retaining pin 7 illustrates one suitable method of securing and adjusting the vertical support 4, 5, any suitable method of securing the two shafts together can be used. Those skilled in the art will also recognize that any suitable material can be used to fabricate the therapeutic lamp assembly 1.

Figure 2:
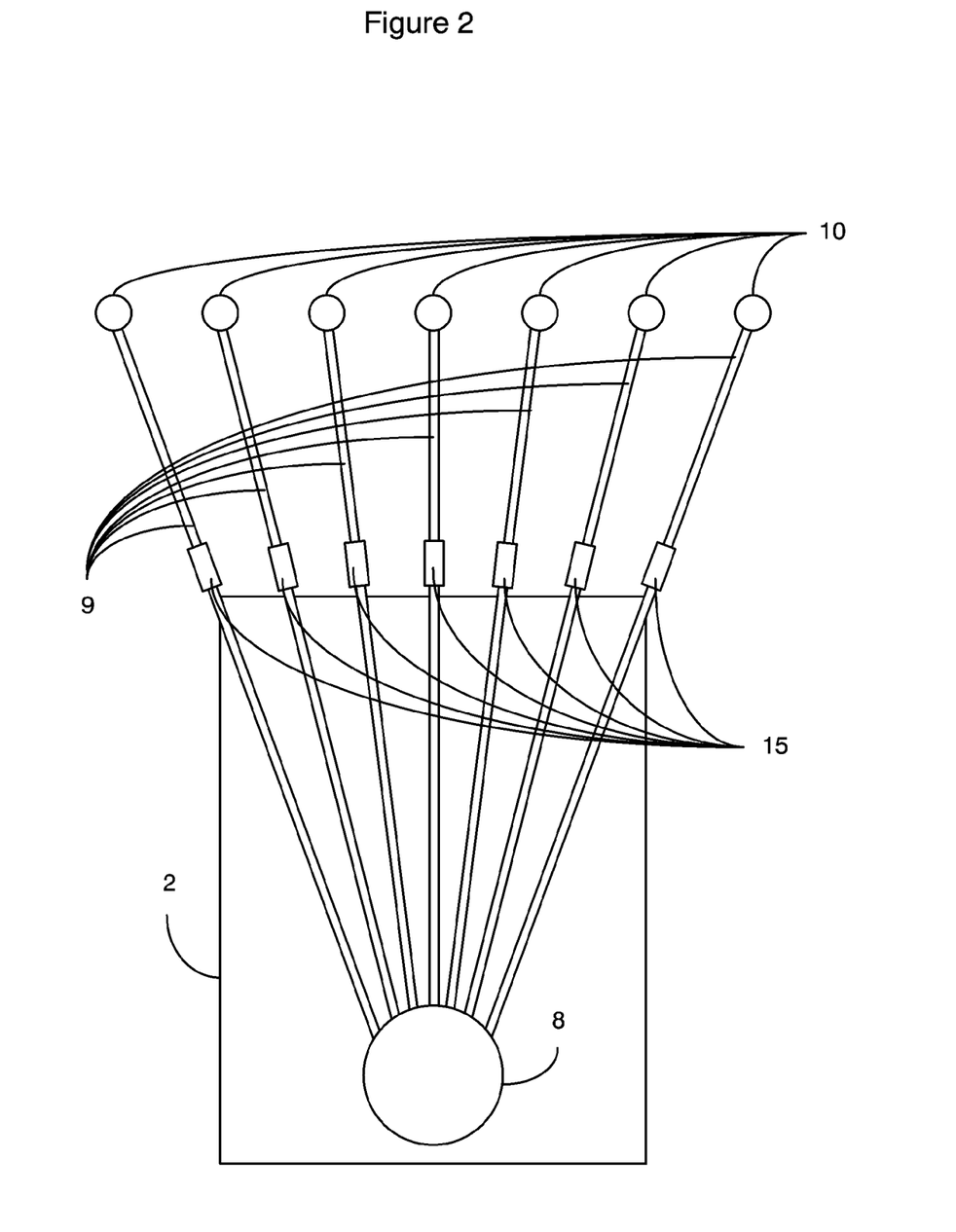
FIG. 2 is a diagram that illustrates a top view of a preferred embodiment of the light therapy device.

In FIG. 2, a top view of a preferred embodiment of the therapeutic lamp assembly 1 is shown. The base section 2 is shown supporting the head unit S via the vertical support 4, 5 (not shown). Extending from the head unit 8 are the lamp antis 9. Each lamp arm 9 is attached at its proximal end to the head unit 8. On the distal end of each lamp arm 9 is a lamp assembly 10. As can be seen in this figure, the length of the lamp arms 9 vary to allow each of the lamp assemblies 10 to align with the other lamp assemblies 10 such that they lie in a substantially straight line. The purpose of the straight line is to allow the light beams emitted by the lamp assemblies 10 to be projected onto chakra points which extend along a line that extends longitudinally through the middle part of the patient's body. Chakra points are well known in the art. While it is possible to have fixed length lamp arms 9 which would suit the average sized person, the use of telescoping lamp arms 9 allows a single therapeutic lamp assembly to be adjusted to accommodate individuals of any size. In this figure, telescoping lamp arm 9 are secured together by optional grips 15. When an individual of a particular size lays down for treatment, the operator would adjust the length of each individual lamp arm 9 via its associated grip 15. Likewise, the angle from which the lamp arm 9 extends from the head unit 8 would also be varied by pivoting the lamp arm 9 at the head unit 8. This will allow precise alignment with the chakra points of an individual patient.

Figure 3:
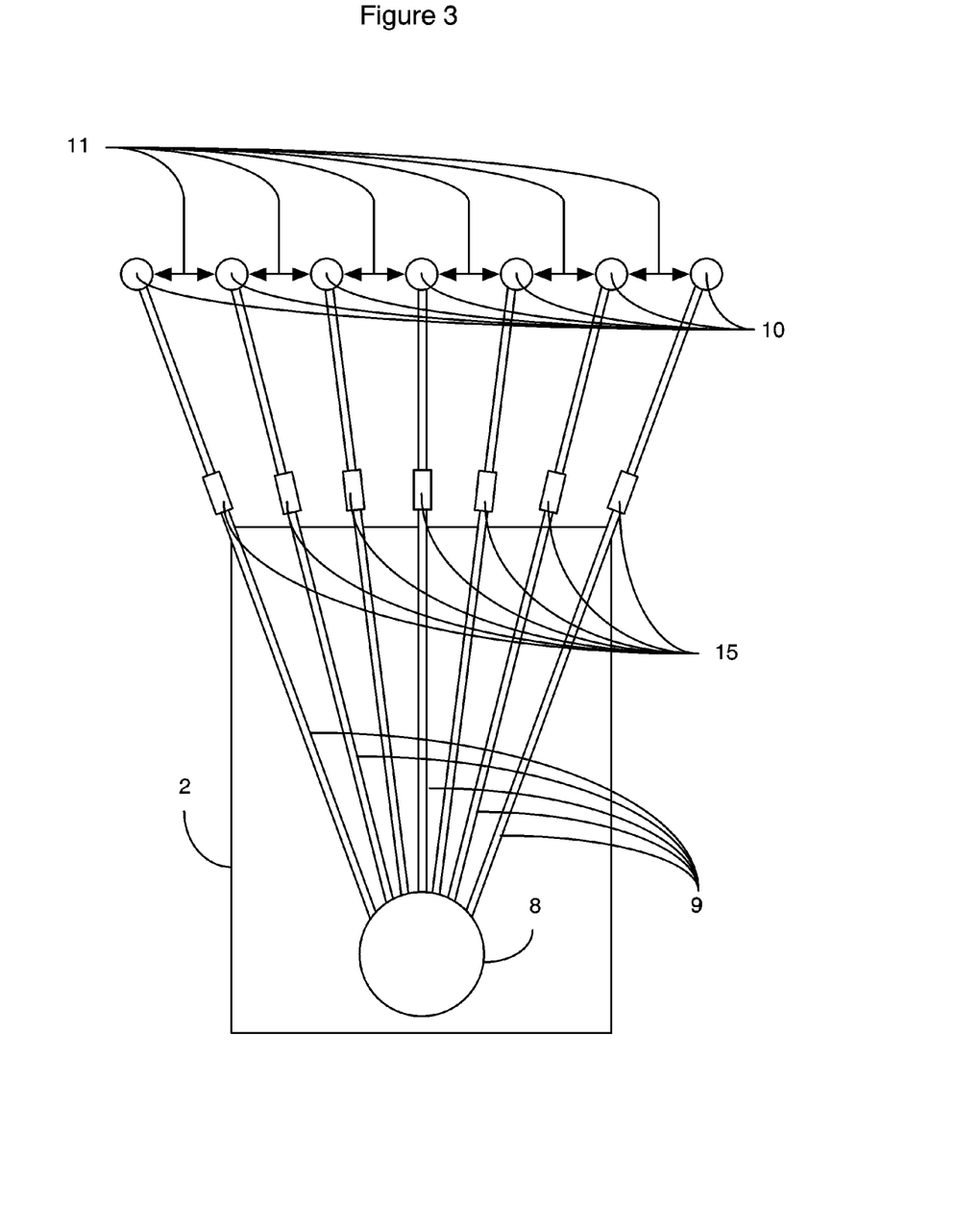
FIG. 3 is a top view of a preferred embodiment of the invention which illustrates spacing between the lamp assemblies.

FIG. 3 illustrates another feature of a preferred embodiment of the therapeutic lamp assembly 1. In this figure, distances 11 between the lamp assemblies 10 are preferably initially set to six inches. This spacing will accommodate individuals of average size. However, those skilled in the art will recognize that individuals of varying sizes will require that lamp arms 9 be adjustable via grips 15. By making lamp arms 9 adjustable, the lamp assemblies 10 can be accurately aligned with the chakra points on individuals of varying size.

Figure 4:
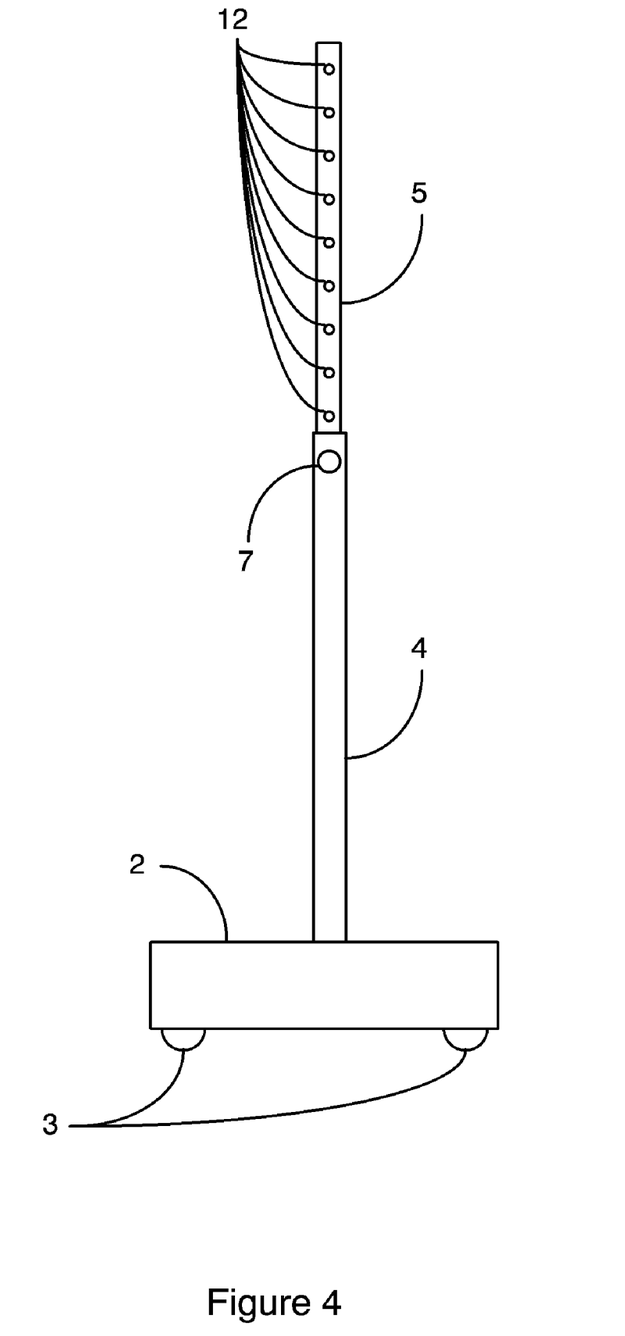
FIG. 4 is a rear view of a preferred embodiment of the invention which illustrates how the upper vertical shaft is inserted into, and secured to, the lower vertical shaft.

In FIG. 4, the rear view of a portion of a preferred embodiment of the therapeutic lamp assembly 1 is shown. In particular, the upper vertical shaft 5 is shown inserted into the lower vertical shaft 4. A series of retaining apertures 12 are shown spaced along the length of the upper vertical shaft 5. In a preferred embodiment, the lower vertical shaft 4 is approximately 40 inches in length, and the upper vertical shaft 5 is approximately 32 inches in length. The retaining apertures 12 are spaced approximately three inches apart. In addition, they are sized such that the retaining pin 7 can be inserted through a selected retaining aperture 12 to secure the upper vertical shaft 5 to the lower vertical shaft 4. In this embodiment, the lower vertical shaft 4 can be a 1.75 inch diameter pole and the upper vertical shaft 5 can be a 1.5 inch diameter pole, both of which are concentrically available. As noted above, telescoping poles such as this are known in the art. In addition, any suitable method of securing two slidable poles together can be used, such as pressure grips, etc. Likewise, any suitable material can be used to fabricate the structural components of the device.

Figure 5:
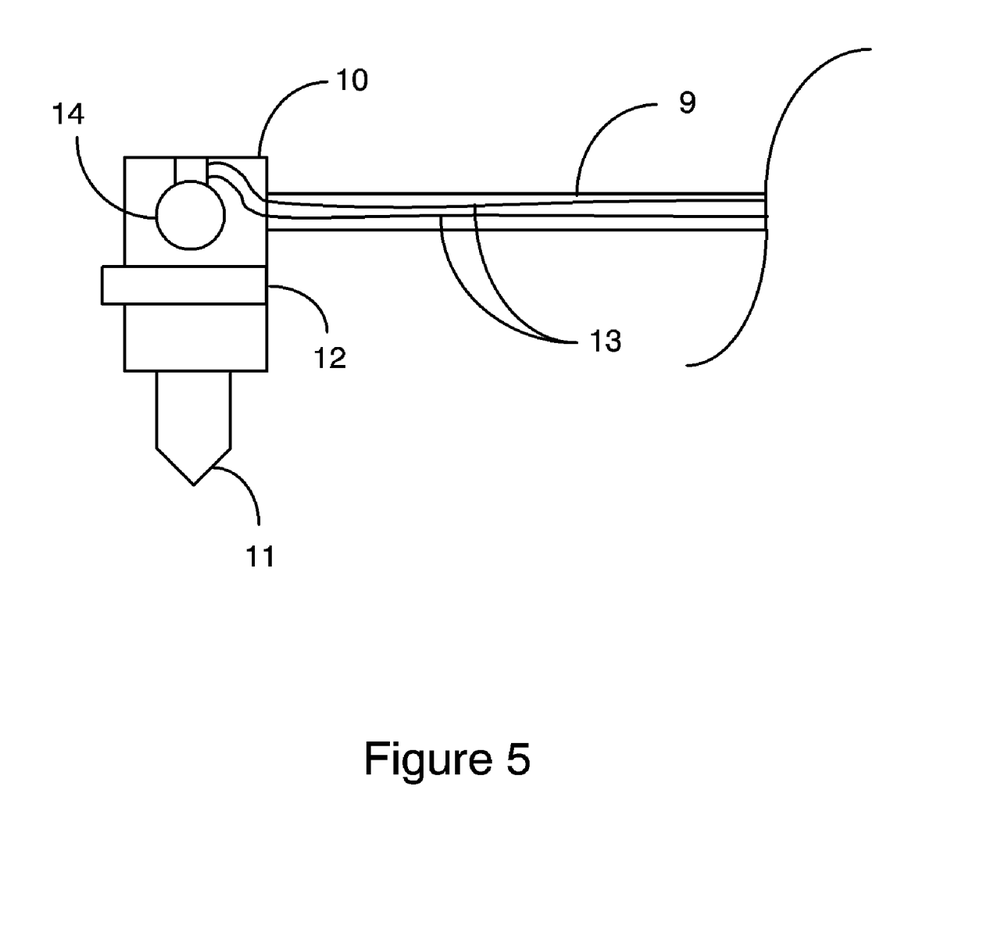
FIG. 5 is a side cut away view of a preferred embodiment of the lamp assembly which is shown attached to a portion of the lamp arm.

In FIG. 5, a preferred embodiment of the lamp assembly 10 is shown. In this cut away view, power lines 13 are shown inserted into the channel defined by lamp arm 9. The power line 13 extends from lamp arm 9 into a lamp assembly 10 where it is attached to the lamp 14. The lamp 14 provides light which is directed at color filter 12. In this figure, the color filter 12 is shown extending slightly from the side of the lamp assembly 10 to better illustrate that it can be removed and replaced with other color filters 12. Once light passes through the color filter 12 it then passes through crystal 11 on its way to the target area on the patient. In the preferred embodiment, it is envisioned that the lamp assembly is removable from the lamp arm 9 such that it can be easily replaced for maintenance purposes. Likewise, crystal 11 is a quartz crystal which is shaped such that it acts as a prism. The shape of the prism is preselected to direct a selected color light to the patient.

Those skilled in the art will recognize that since the crystal 11 is used as a prism, any suitable material can be used to fabricate it in addition to quartz.

The base section 2 can also include a optional processor to automatically control the sequencing of the lamp assemblies 10, and the selection of colors projected by the lamp assemblies 10. This can be easily accomplished by a small motor assembly to rotate the color filters 12 which can be structured to hold several different color sections. Likewise, a motor assembly in the lamp assembly 10 can also be used, under program control by the processor in the base section 2, to rotate the crystal 11 to another prism point on the crystal 11 which will direct a different color to the patient's body. Of course, the processor would preferably be programmable to allow the light therapy to be programmed for a specific patient.

Figure 6:
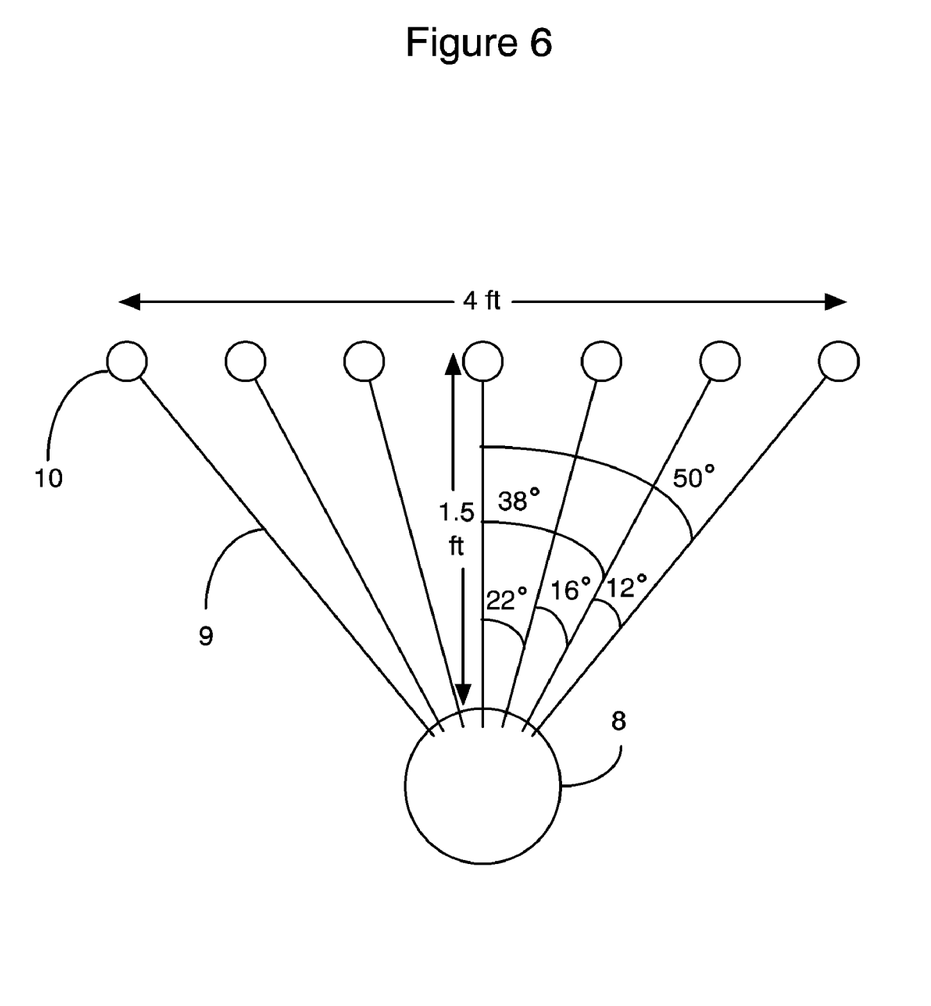
FIG. 6 is the top view of a preferred embodiment which illustrates how the lamp assemblies can be aligned.

FIG. 6 illustrates another preferred embodiment which shows how lamp assemblies 10 may be aligned. In this figure, the central lamp assembly 10 extends 18 inches outward from the head unit 8. A lamp arms 9 which are adjacent to central lamp assembly are angled away from the lamp assembly by 22 degrees. Likewise, the lamp arms 9 which are adjacent to those lamp arms 9 are angled at 16 degrees, and the lamp arms 9 which are adjacent to that set of lamp arms 9 are angled at 12 degrees from there are adjacent lamp arms 9. By adjusting the lamp arm 9 lengths such that the lamp assemblies 10 are in a substantially straight line, the lamp assemblies 10 covered area of approximately four feet which is adequate to provide light therapy to a typical adult.

The blinking and frequency sequence used by the therapeutic lamp 1 is as follows:

1. Assuming that there are seven lamp assemblies 10 arranged in order and denominated as lamps 1 through 7. All of the frequency groups may share the same frequency, or may use a particular frequency, represented by a specific color, for each frequency group, the frequency groups associated with each lamp are as follows:
   a. Frequency group 1: The frequency in this group is associated with lamp assemblies 1 and 3.
   b. Frequency group 2: The frequency in this group is associated with lamp assemblies 5 and 7.
   c. Frequency group 3: The frequency in this group is associated with lamp assemblies 2, 4 and 6.

2. The blinking sequence of the frequency groups is as follows:
   a. Group 1
   b. Group 2
   c. Group 1
   d. Group 3
   e. Group 1
   f. Group 3
   g. Group 1
   h. Group 2
   i. Group 1

3. In the preferred embodiment, the frequency groups are timed to remain activated for 3 seconds each. However, the length of time is not critical and can be varied.

While the invention has been described with respect to a preferred embodiment thereof, it will be understood by those skilled in the art that various changes in detail may be made therein without departing from the spirit, scope, and teaching of the invention. For example, the materials used to fabricate the structural support elements of the device can vary, the material used to fabricate the crystal can vary, number of lamps can vary, etc.

I claim:

1. An apparatus for applying light therapy, comprising:
a base section, the base section further comprising:
control circuitry; and
power supply means;
an adjustable vertical support attached at its lower end to the base section;
a head unit attached to the upper end of the vertical support;
a plurality of lamp arms attached at their proximal end to the head unit and extending from the head unit;
a plurality of lamps, each lamp attached to the distal end of a lamp arm;
means to control activation of individual lamps in a predetermined sequence; and
means to control the light color output by each of the individual lamps.

2. An apparatus, as in claim 1, further comprising:
means to direct the light emitted by the lamps to specific chakra points on the body of a patient using the apparatus.

3. An apparatus, as in claim 2, further comprising:
means to pulse the lamps intermittently in a predetermined pattern.

4. An apparatus, as in claim 3, further comprising:
means to periodically select a color from a predetermined selection of colors, and to project that color from a lamp.

5. An apparatus, as in claim 4, further comprising:
means to use a prism as a primary color filter to filter the light color from the lamp.

6. An apparatus, as in claim 5, further comprising:
a secondary optical color filter to filter the light from the lamp.

7. An apparatus, as in claim 5, wherein:
there are seven lamp assemblies arranged in order and denominated as lamps 1 through 7;
the lamps are divided among three frequency groups, the frequency groups all share the same frequency, or each lamp or subset of lamps is part of a particular frequency group, represented by a specific color for each frequency group, the frequency groups further comprising:
frequency group 1 is associated with lamp assemblies 1 and 3;
frequency group 2 is associated with lamp assemblies 5 and 7; and
frequency group 3 is associated with lamp assemblies 2, 4 and 6; and
means to sequentially activate the lamps in a frequency group as follows:
group 1, then group 2, then group 1, then group 3, then group 1, then group 3, then group 1, then group 2, then group 1.

8. An apparatus, as in claim 5, further comprising:
programmable means to control sequencing of the frequency groups.

9. An apparatus for applying light therapy, comprising:
a base section, the base section further comprising:
control circuitry;
power supply means;
a vertical support attached at its lower end to the base section;
the head unit attached to the upper end of the vertical support;
a plurality of lamp arms attached at their proximal end to the head unit and extending from the head unit;
a plurality of lamps, each lamp attached to the distal end of a lamp arm;
means to control activation of individual lamps in a pre-determined sequence;
means to control the light color output by each of the individual lamps; and
means to direct the light emitted by the lamps to specific chakra points on the body of a patient.

10. An apparatus, as in claim 9, wherein:
the vertical support is adjustable in length;
the lamp arms are adjustable in length;
the angle of the lamp arms in relation to one another are adjustable means to activate the lamps having predetermined colors in a predetermined sequencing pattern.

11. An apparatus, as in claim 10, further comprising:
means to pulse the lamps in a predetermined timing pattern.

12. An apparatus, as in claim 11, further comprising:
programmable means to control color and/or pulse timing sequencing.

13. An apparatus, as in claim 12, further comprising:
means to use a prism as a primary color filter to filter the light color from the lamp.

14. An apparatus, as in claim 13, further comprising:
a secondary optical color filter to filter the light from the lamp; and
a quartz crystal is used as the prism.

15. An apparatus, as in claim 12, wherein:
there are seven lamp assemblies arranged in order and denominated as lamps 1 through 7;the lamps are divided among three frequency groups, the frequency groups all share the same frequency, or each lamp or subset of lamps is part of a particular frequency group, represented by a specific color for each frequency group, the frequency groups further comprising:
frequency group 1 is associated with lamp assemblies 1 and 3;frequency group 2 is associated with lamp assemblies 5 and 7; and
frequency group 3 is associated with lamp assemblies 2, 4 and 6; and
means to sequentially activate the lamps in a frequency group as follows:
group 1, then group 2, then group 1, then group 3, then group 1, then group 3, then group 1, then group 2, then group 1.

* * * * *